United States Patent [19]

Paluch

[11] 4,333,451
[45] Jun. 8, 1982

[54] POSITIVE PRESSURE BREATHING APPARATUS WITH CONDENSATE REMOVAL

[76] Inventor: Bernard R. Paluch, 1607 Cedar La., Mt. Prospect, Ill. 60056

[21] Appl. No.: 215,832

[22] Filed: Dec. 12, 1980

[51] Int. Cl.³ .............................................. A61M 16/00
[52] U.S. Cl. ........................... 128/205.12; 128/205.24; 128/911
[58] Field of Search ................... 128/205.12, 204.18, 128/205.24, 911

[56] References Cited

U.S. PATENT DOCUMENTS

| 1,824,512 | 9/1931 | Szamier | 128/911 |
| 4,007,737 | 2/1977 | Paluch | 128/911 |
| 4,249,527 | 2/1981 | Ko et al. | 128/205.24 |

FOREIGN PATENT DOCUMENTS 520342  7/1920  France ............................. 128/911

OTHER PUBLICATIONS

Respiratory Technology Corp., SCCR "Synchronized Continuous Condensate Removal" Ventilator Breathing Circuit-Brochure.

Primary Examiner—Henry J. Recla
Attorney, Agent, or Firm—Darbo & Vandenburgh

[57] ABSTRACT

The conditioned air from a ventilator enters one chamber in a manifold, which chamber has a connection to an inspiratory conduit through which the conditioned air is conducted to the patient. The expiratory conduit from the patient communicates in the manifold with a second chamber, positioned below the first chamber. A wall in the manifold at the lowermost part of the first chamber defines an orifice providing fluid communication between the two chambers. At the lower part of the second chamber is the expiratory valve which is pulsed by the ventilator. Adjacent the patient is a slanted "Y" and elbow which provide communication between the inspiratory conduit, the expiratory conduit, and the patient's single endotracheal or tracheostomy tube. Various ports are provided in the "Y" and elbow and are closed by caps. These ports provide connections suitable for various needs such as temperature measurement, ventilator temperature controller probe, etc. In one embodiment the connections at the elbow provide freedom of rotational movement in two planes, which planes are at approximately right angles to each other. Various other features are incorporated to facilitate use of the ventilation apparatus to meet diverse requirements.

18 Claims, 6 Drawing Figures

POSITIVE PRESSURE BREATHING APPARATUS WITH CONDENSATE REMOVAL

BACKGROUND AND SUMMARY OF THE INVENTION

In the positive pressure breathing treatment of a patient a pulse of air is forced into the patient's lungs and with the termination of the pulse the patient exhales. To accomplish this, a breathing circuit is connected between the patient and a ventilator. The ventilator produces and times the pulses as well as conditions the air supplied to the patient, such conditioning primarily being a matter of increasing temperature and humidity of the air. The patient end of the breathing circuit is connected to an endotracheal or tracheostomy tube located in the patient. Since both of these tubes by-pass the patient's upper airway, it is necessary that the air being supplied to the patient be properly conditioned so as to provide to the lungs temperature and humidity levels comparable to that provided by the upper airway. It is customary for the ventilator to deliver air into the circuit saturated with water, and at a temperature such that by the time the air has passed through the circuit to the patient, with the resulting heat losses, it will be received by the patient at approximately body temperature. As the air moves through the circuit to the patient from the ventilator the reduction in air temperature reduces the quantity of moisture that the air can hold at one hundred percent relative humidity, and the excess moisture condenses out as liquid water. The term "air" is used herein to refer to the gas that is supplied to the patient for breathing purposes. That gas is not necessarily identical to the ambient atmosphere, since the percentages of oxygen, nitrogen, etc., may be adjusted or enriched to accommodate the requirements for the treatment of a particular patient.

Such condensate is troublesome. If allowed to collect it can reduce the effective cross-sectional area (lumen) of the inspiratory conduit available for transmitting air to the patient. The use of a condensate collection bottle on the inspiratory side is undesirable for a number of reasons which include: (a) it increases the compressible volume of the system necessitating an increase in the total volume of gas that the ventilator must deliver, which in turn adversely affects the determination of physiological parameters such as static and dynamic lung compliances; (b) the volume and weight of such a condensate container adds to the problems of bulk and creates a requirement for increased support of the ventilation circuit; (c) such a collection container can become a site for bacterial growth; and (d) emptying the collection bottle interrupts the ventilation of the patient. My prior U.S. Pat. Nos. 3,865,106 and 3,945,378 relate to ventilation circuits which incorporate the feature of placing the inspiratory conduit concentrically within the expiratory conduit to thereby reduce the heat loss of the inspiratory conduit to the end that less condensate will occur in the inspiratory conduit. While such arrangement can reduce the amount of condensate in the inspiratory conduit it does not eliminate it.

A principal object of the present invention is to provide a ventilation circuit between the patient and the ventilator which is effective in removing condensate from the inspiratory conduit without the disadvantages associated with a condensate bottle interposed directly in the inspiratory conduit, and without any deleterious effects on the normal operation of the ventilation circuit. Incidentally, the term "ventilator" is used herein to include all of the various types of apparatus for supplying the conditioned air and pulsing the circuit with positive pressure inhalation pulses separated by exhalation periods. Such devices are sometimes referred to as respirators, positive pressure machines, or volume ventilators, and the present invention is equally applicable thereto.

Another feature of the present invention is that the manifold through which the condensate removal takes place is at the ventilator end of the circuit and can in fact be supported directly by the ventilator. This, plus the fact that the exhalation valve which is pulsed by the ventilator is a part of that manifold, is quite advantageous. In contrast to this, conventional circuits will have the exhalation valve at some location about midway of the ventilation circuit. Since this generally is a fixed location and is a point requiring support because of the presence of the valve, it is a limiting factor in the physical accommodation of the circuit to the specific needs of the individual patient. The elimination of this limiting factor can be a great advantage in the ability of the medical personnel to accommodate the circuit to the needs of the patient, to the end of achieving the greatest patient comfort, etc. Furthermore, this change provided by the present invention permits the arrangement of both the inhalation and exhalation conduits in a manner such that the condensate in each will flow downhill throughout the lengths of the conduits to the ends connected to the ventilator mounted manifold.

As in the prior art devices, the inhalation and exhalation conduits communicate with each other and with the patient's endotracheal or tracheostomy tube at a fitting located close to the patient. In contrast to the prior art, however, in the present invention the other ends of the inhalation and exhalation conduits enter a manifold located immediately adjacent the ventilator. In this manifold there are separate inhalation (inspiratory) and exhalation (expiratory) chambers, the inhalation chamber being generally above the exhalation chamber. The air supply from the ventilator communicates with the inhalation chamber. The exhalation control valve is put in the lowermost part of the exhalation chamber, with a fluid discharge connection on the manifold, below that valve and communicating with the valve. A lowermost part of the dividing wall between the inhalation chamber and the exhalation chamber has an orifice therein. While the liquid condensate in the inhalation chamber will drain through this orifice into the exhalation chamber for ultimate discharge through the valve and the discharge connection, the airflow in the circuit to and from the patient is essentially unaffected by the existence of this orifice, i.e., for all practical purposes no airflow through the orifice occurs in the inspiratory or expiratory portions of the breathing cycle. This is due to the fact that during these portions of the breathing cycle the inspiratory and expiratory conduits are in communication with each other at the ends thereof adjacent the patient and because of this connection the air pressures in the two conduits, and thus in the two chambers in the manifold are essentially equal. Since the air pressure on each side of the orifice is essentially equal there is no significant air flow through the orifice. Thus the presence of the orifice fails to have any deleterious effect on the breathing cycle produced by the ventilator and the ventilation circuit. Since both the inspiratory and expiratory conduits may be arranged to drain downhill to the manifold, the condensate which develops in each will drain into the manifold and, during the times that the exhalation valve is open, will pass through that valve to the discharge connection on the manifold. A collection container or bottle is connected to this discharge connection to receive such condensate and other liquid from the system. When full, it may be disconnected and emptied without in any way interfering with the positive pressure ventilation of the patient.

Other features of the invention will be apparent from the following description as well as the role played thereby in providing a ventilation circuit apparatus which is easily accommodated to meet the needs in the treatment of a patient under the individual circumstances present in that patient's treatment.

DESCRIPTION OF SPECIFIC EMBODIMENTS

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

Figures 1, 2, 3, 4:
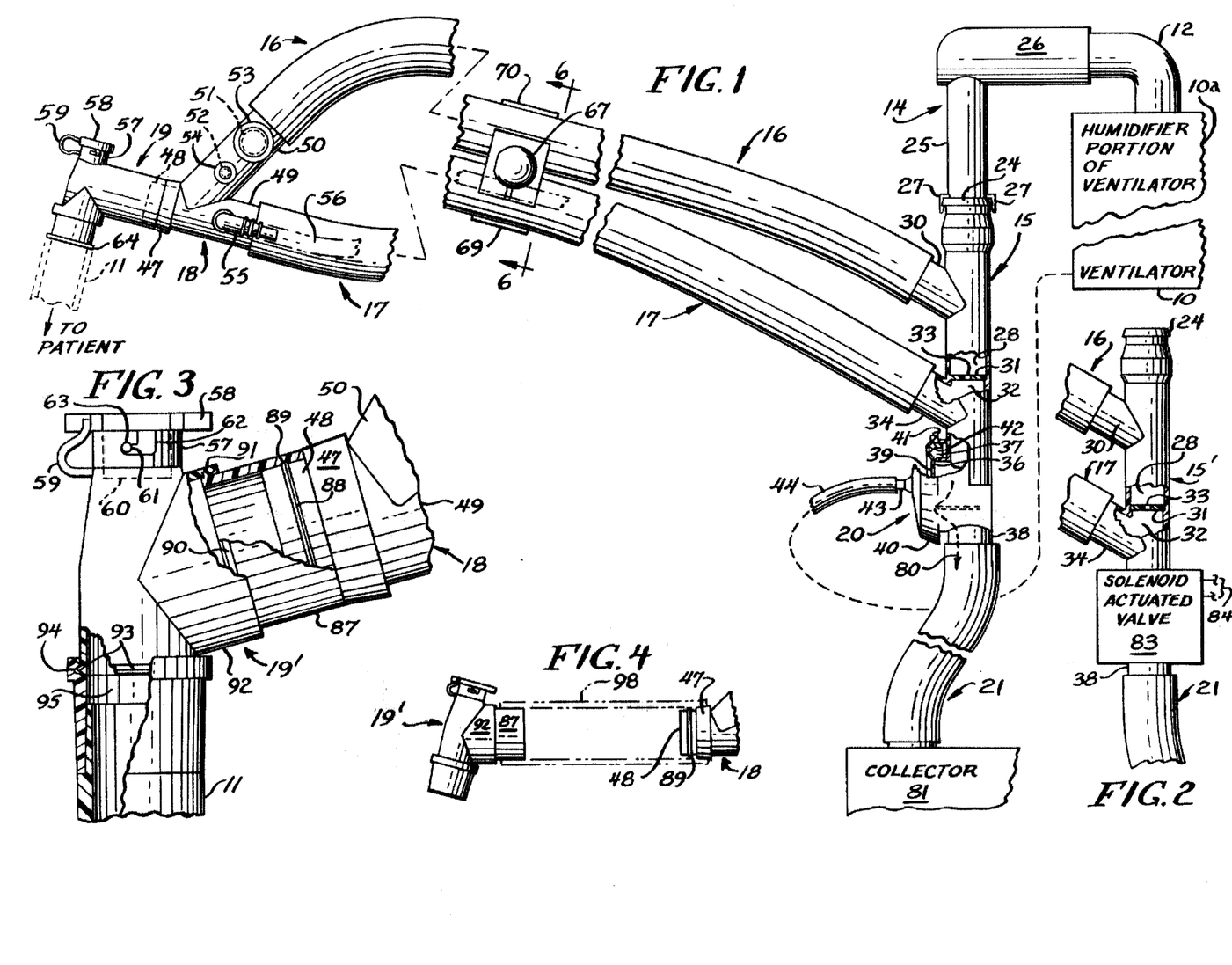
FIG. 1 is an elevational view, partially in section, of a ventilation circuit embodying the present invention.
FIG. 2 is a partial view of the circuit of FIG. 1 in which an alternative form of exhalation valve is employed.
FIG. 3 is an elevational view, partially in section, of an alternative form of elbow employed at the patient end of the circuit.
FIG. 4 is a view illustrating the manner in which the elbow of FIG. 3 may be employed to incorporate a "dead space" in the patient's breathing circuit.

Referring to FIG. 1, a ventilation circuit is employed between a conventional ventilator 10 and a tube 11 leading to the patient's respiratory system. Such a tube may be an endotracheal or tracheostomy tube, or the tube may be replaced by a mask fitted over the patient's face in emergency equipment. The air to be supplied to the patient is heated and humidified in a humidifier portion 10a of the ventilator, and after being so conditioned, passes into the ventilator circuit through a ventilator air-supply conduit which in the illustrated embodiment is represented by an elbow 12. In some ventilators this air-supply conduit may not be in the form of an elbow, and if its distal end is not in the form of a horizontal conduit, as is the case with respect to the illustrated elbow, a fitting such as elbow 12 is added to permit the manifold of the present invention to be supported therefrom.

The ventilation circuit illustrated in FIG. 1 employs an air-supply conduit, generally 14, a manifold, generally 15, an inspiratory or inhalation conduit, generally 16, an expiratory or exhalation conduit, generally 17, a "Y" at which the two conduits communicate, generally 18, a patient elbow, generally 19, an exhalation valve, generally 20, and an exhaust or discharge conduit, generally 21. The conduits 16, 17 and 21 are formed of conventional flexible plastic tubing. While they are illustrated as being smooth-walled in form, such conventional tubing often is of a corrugated form to increase the flexibility of the tubing. Various components making up the elements of the circuit might be disposable in character or might be made for reuse (after suitable sterilization).

The manifold 15 is generally in the form of a vertical column or tube. At its upper end this tube has an annular ridge 24, the exterior of which is in the form of a truncated cone. This upper end forms an intake or air-supply connection and to this end it is dimensioned to telescopically receive the vertical leg 25 of the elbow forming the air-supply conduit 14. This elbow has a horizontal leg 26 dimensioned to telescopically fit over the elbow 12 of the ventilator. Leg 25 of the air-supply conduit has a pair of clips 27 which extend about and engage the underside of the annular ridge 24 of the manifold. Thus the air-supply conduit (elbow) 14 supports the manifold from the ventilator, while permitting the manifold to be rotated about a vertical axis as may be required. The clips 27 may be manually pushed outwardly at their distal ends to thereby disengage the manifold from the air-supply conduit and allow them to be telescopically separated. of course, other means of making these connections are possible, and the instant design is but one embodiment useful to this end.

The internal tubular opening that receives the air-supply conduit 14 also forms the inhalation chamber 28 of the manifold. A tubular portion 30 communicates with this inhalation chamber and extends upwardly and outwardly from the vertical part of the manifold. This tubular portion forms a connection for the inspiratory conduit 16. A transverse wall 31 in the manifold separates the inhalation chamber 28 from an exhalation chamber 32. Wall 31 defines an orifice 33 which permits fluid communication between the two chambers. A tubular portion 34 communicates with the exhalation chamber 32 and extends upwardly and outwardly therefrom. It forms a connection for the expiratory conduit 17.

The lower end of the exhalation chamber 32 extends outwardly in a horizontal direction to one side (to the left in FIG. 1) and terminates in an annular valve seat 36. Surrounding this valve seat is a space 37 which is in communication with the discharge conduit connection 38 of the manifold. A flexible diaphragm 39 overlies the valve seat. The periphery of the diaphragm is held between a cover 40 on one side and a rim 41 and annular insert 42 on the other side. The cover 40 has fingers (not shown) which engage about rim 41 and securely lock the cover to the manifold body to prevent tampering with the valve and to hold the diaphragm firmly in place. Within the cover and between it and the diaphragm is an air chamber which communicates with a control connection 43 on the cover. The diaphragm normally lays loosely against the valve seat so that, in the absence of air pressure being supplied through hose 44 the valve acts as a check valve; i.e., it permits air flow from the expiratory chamber to the discharge-conduit connection while blocking air flow in the reverse direction. With air pressure supplied to the valve through hose 44 the diaphragm is thereby pressed against the seat to block the flow through the valve in either direction. A hose 44 is used between connection 43 and the ventilator 10.

Adjacent the patient, the inspiratory and expiratory conduits communicate with each other at the "Y" 18. This "Y" has a trunk portion 48 with a collar 47 there-about and two arm portions 49 and 50. The "Y" is irregular (or offset) in the sense that the trunk portion 48 and the arm portion 49 are concentric about a common axis, with the arm portion 50 extending outwardly (and upwardly) from that axis. The inspiratory conduit 16 connects to the upwardly extending arm 50 while the expiratory conduit 17 connects to the arm 49. This offset "Y" has several advantages. It provides a straight flow of the exhaled air from the patient, thus minimizing the resistance to that air flow. Also, any condensate in the exhalation path will normally be directed into the exhalation conduit. There is substantially no opportunity for that condensate, or any ejected secretions, etc., that may be present, to get into the inhalation conduit, in contrast to the bifurcated "Y's" now commonly used.

Extending out sidewise from the arm portion 50 (toward the viewer in FIG. 1) are two tubes 51 and 52 which define ports. These are normally closed by caps 53 and 54, as shown in FIG. 1. The port of tube 51 allows the insertion of a thermometer (124 in FIG. 5) when the cap is removed, thereby permitting personnel to observe the temperature of the air at that location closely adjacent the patient. The port of tube 52 is provided to permit, when desired, the insertion of a temperature control probe (125 in FIG. 5) connected to ventilator 10 for automatically adjusting the air temperature exiting from the ventilator to the end that it is maintained at a given desired temperature when arriving at the patient "Y" 18. Projecting toward the viewer in FIG. 1 is an elbow 55 to receive tubing 56 connected to a conventional airway pressure monitor on the ventilator 10. The patient elbow 19 has a tube 57 forming a port coaxial with the tube 11 leading to the patient. This port is normally closed by a cap 58 held captive by a connecting strap 59. The cap has a central plug 60 which is received within tube 57 to close the port when the cap is in place. Ears 61 extend outwardly from this plug to project into slots 62 in tube 57 and thereby lock the cap to the tube (see particularly FIG. 3). At the closed ends of the slots, the configuration is such as to form detents 63 so as to lock the ears in place against accidental displacement. With the significant force developed by intentional twisting of the cap, the ears will slide past the detents to permit removal of the cap. At the end of the elbow to which the tube 11 to the patient is affixed is a collar 64. Some tubes 11 are larger than usual, and thus do not fit in the manner illustrated in FIG. 3. Collar 64 provides an attachment and seal for these larger patient tubes to fit on the outside of this end of the elbow.

Figures 5, 6:
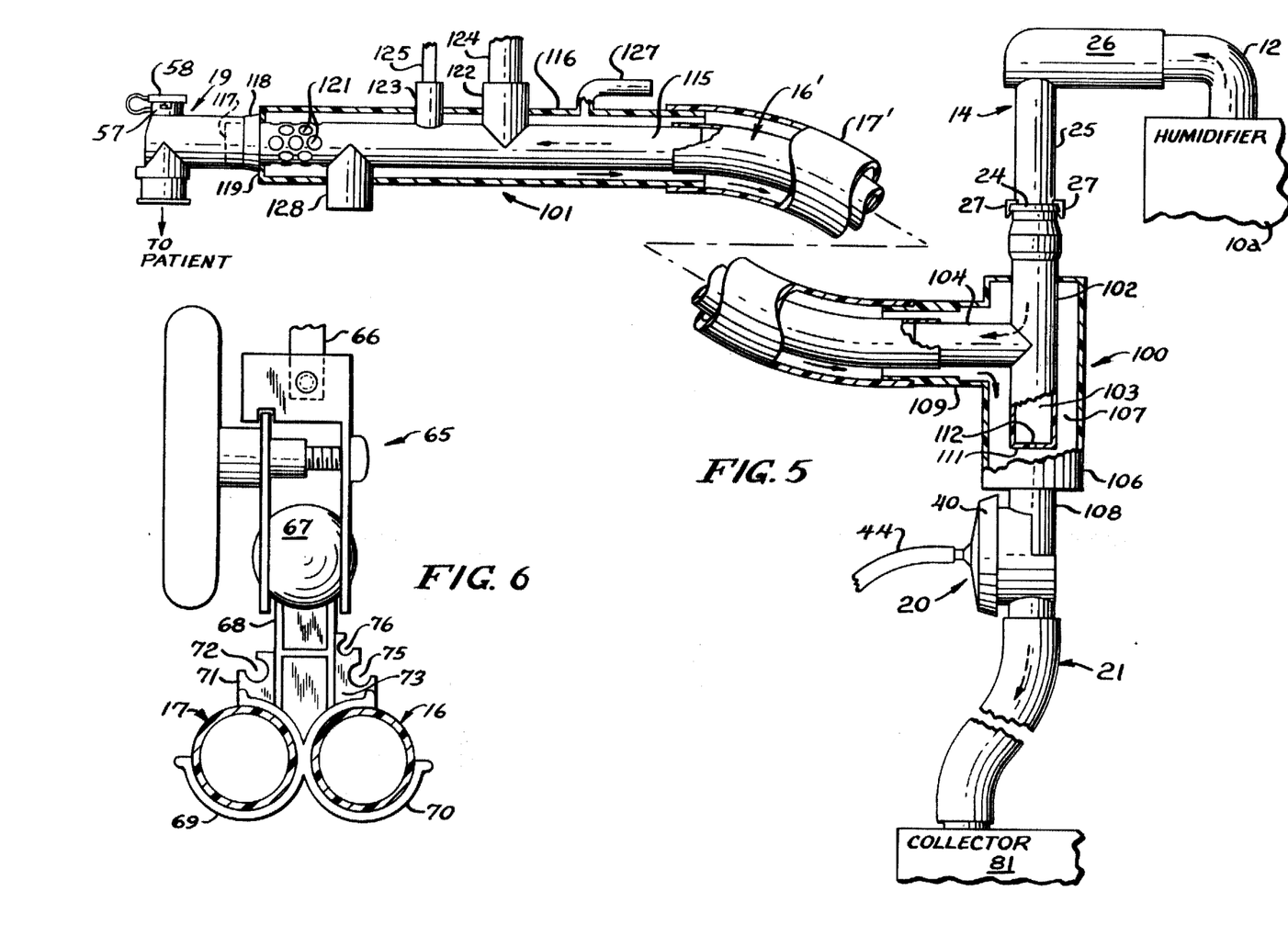
FIG. 5 is an alternative embodiment for use of the invention with a breathing circuit wherein the inspiratory and expiratory conduits are concentric.
FIG. 6 is a sectional view as seen at line 6—6 of FIG. 1.

FIGS. 1 and 6 illustrate an adjustable support for the conduits 16 and 17. It is intended to be connected to a conventional universal clamp mechanism, generally 65, which is employed on the distal end of a series of interconnected support arms 66 in the conventional apparatus. As is the case with the conventional apparatus, my tubing support employs a spherical head 67 of a size to be engaged by the clamp mechanism 65. A post 68 connects head 67 to a pair of tubing clips 69 and 70. These components are formed of a molded plastic and the clips have sufficient flexibility so that they may be pressed open to receive the respective conduits 16 or 17. Normally they will frictionally engage the conduits. However, they will slide lengthwise of the conduits thereby permitting the positioning of the support to be varied along the length of the conduits as required. A web 71 at one side of post 68 has an opening 72 of a size suitable to allow the tubing 56 to be snapped therein and held by the tubing support. A web 73 at the opposite side of the post has an opening 75 for similarly holding other similar signal transmitting members. For the embodiment of FIG. 5 (hereinafter described) a similar support would be employed, but with but a single tubing clip (69 or 70) sized to engage conduit 17'.

To those familiar with the practice it will be readily apparent that the ventilation circuit of FIG. 1 operates to induce breathing in the patient in a conventional manner. As the ventilator produces a pulse of air to inflate the patient's lungs, it also produces a timed control pulse through hose 44 to close the exhalation valve 20 by pressing the flexible diaphragm 39 against the valve seat 36. As the pressure pulse of air is transmitted from elbow 12 of the ventilator, through the inhalation chamber 28 of the manifold, the inspiratory conduit 16, etc., it also creates a pressure in exhalation chamber 32 of the manifold which is essentially equal to the pressure in the inhalation chamber 28. That is, the internal dimensions (lumens) of the two conduits 16 and 17 and the connecting "Y" 18 therebetween are of a magnitude such that they present no significant resistance to the airflow. For that reason the instantaneous pressure throughout these members and thus in the two chambers 28 and 32 is substantially equal. However, the orifice 33 defines such a small passageway (e.g., 0.060 in. or 1.524 mm in diameter and length) that it has a relatively high resistance to airflow, as compared to the lack of resistance through the conduits. The result of these comparative resistances is that there is substantially no airflow through the orifice 33 during the inspiratory phase of the respiratory cycle.

The same effect occurs during the exhalation phase of the respiratory cycle. With the inhalation pulse being discontinued by the ventilator, the ventilator also removes the air supplied to pressurize the diaphragm of valve 20 and the valve opens. The patient now exhales, with the exhalation flow of air being through conduit 17, valve 20 and discharge conduit 21. Again, due to the lack of resistance in conduits 16 and 17 and the connecting "Y" 18, the pressure in chambers 28 and 32 is essentially equal, but there is a significant resistance present at orifice 33. Thus, there is no significant outflow of air into or through the conduit 16, it all being through the exhalation conduit 17.

Preferably, the personnel will arrange the ventilation circuit so that the patient "Y" 18 is at a relatively high elevation, while the manifold 15 is at a relatively low elevation, with there being a gradual slope downwardly from the "Y" to the manifold. Thus the condensate, along with any boluses of phlegm, etc., that may be present in the conduits, will drain from the patient end of the circuit to the manifold 15. All such liquid that is received in the inhalation chamber 28 drains through orifices 33 by gravity. The liquid in the exhalation chamber 32 will likewise flow by gravity through the valve 20, when the valve is open, in the manner illustrated in the dashed line 80. A suitable collection container 81 is employed to receive this liquid. Such a container must also be open to atmosphere so that as the patient exhales the exhalation gases pass to atmosphere without resistance. Should the collector 81 become filled, it can be removed and emptied or replaced without the ventilation cycle being interrupted in the slightest, since it is connected into the circuit downstream of the exhalation valve 20.

FIG. 2 illustrates a modification wherein the fluid actuated valve 20 of FIG. 1 is replaced by a solenoid actuated valve 83. Otherwise the components of the manifold 15' of FIG. 2 correspond to the components of the manifold 15 of FIG. 1. A pair of wires 84 connect the solenoid of valves 83 to appropriate circuitry in the ventilator 10 to time the opening and closing of the valve 83 in a manner corresponding to the timing of the opening and closing of the valve 20 of FIG. 1.

FIG. 3 illustrates a modified patient elbow 19', the modifications being such as to provide freedom of rotation in two planes disposed approximately at right angles to each other. Here there is a sleeve 87 which at one end receives the trunk portion 48 of the patient "Y" 18. As is the case with the embodiment of FIG. 1, but not shown therein, the trunk portion 48 has an annular ridge 88 suitably sized and positioned to be received in a groove 89 in the sleeve when the collar 47 is abutting the distal end of the sleeve. At the other end the sleeve has a projecting annular ridge 90 which is received in an annular groove 91 in a transition portion 92 of the elbow. Not only may the trunk portion of the "Y" be rotated with respect to the sleeve 87 (albeit with some drag), but the sleeve 87 is freely rotatable in the transition portion thereby giving one freedom of movement in the plane of the ridge 90. At the other end of the elbow there is a peripheral ridge 93 which is received in a groove 94 in a tubing connector member 95. Thus the connector member is free to rotate in the plane of ridge 93, which plane is nearly at right angles to the planes of rotation incorporated into the sleeve 87. The tubing connector member is sized to receive and engage an adapter which is on the end of, and part of, the tubing 11 leading to the patient. It is highly desirable that the medical personnel arrange the ventilator circuit so as to cause the least discomfort, etc., to the patient. The ability of the personnel to do this is greatly facilitated by elbow 19' in providing relatively free rotational capability in two transverse planes.

One advantage of the embodiments herein described is that there is a minimum of mechanical "dead space" in the circuit. Dead space is a volume in a section of the conduit leading to the patient through which both the inhaled air and the exhaled air passes. Thus during exhalation there will be an accumulation of air enriched with exhaled carbon dioxide in that conduit section. When inhalation takes place that accumulated carbon dioxide returns to the patient. To some extent, this is advantageous since the carbon dioxide induces the patient to breathe more deeply. However, obviously, the patient must be supplied with oxygen and not merely have his/her own carbon dioxide returned. By keeping the dead space to a minimum, there will be a minimum amount of carbon dioxide returned to the patient during each breathing cycle. While conditions will vary from patient to patient, the medical personnel may decide that a particular patient requires more carbon dioxide in the inhalation part of the cycle. To do this, dead space is added to the ventilation circuit. While it is comparatively easy to add dead space, it may be difficult to reduce it. Thus the incorporation of a minimum amount of dead space is advantageous.

FIG. 4 illustrates the ease with which dead space may be added into the circuit of the present invention. The dot-dash lines 98 represent a section of conventional flexible conduit, similar to that employed for conduits 16 and 17, for example, The exterior of a sleeve 87 is of a size only slightly larger than the interior diameter of the conduit used for tubing 98. Similarly, the exterior diameter of collar 47, which is but one manner of creating a tube receiving means, of the patient "Y" 18 is only slightly larger than the interior diameter of the conduit 98. Thus, to add dead space to the ventilation circuit, the medical personnel would cut a piece of conduit 98 to a length to give the desired additional dead space. That piece of conduit would then be slipped onto sleeve 87 and collar 47 in the manner illustrated in FIG. 4. Thereby the conduit 98 would connect the patient elbow 19' with the patient "Y" 18 and provide a dead space through which both the exhaled and inhaled air must traverse. The exterior of the elbow 19 of FIG. 1 immediately adjacent the collar 47 is similarly sized to receive and engage a section of conduit in the manner illustrated in FIG. 4 with respect to the elbow 19'. With the conduit 98 in place, the sleeve 87 is still free to rotate in the transition portion 87, thus maintaining the freedom of rotation in two planes as described in connection with FIG. 3.

As previously mentioned herein, my prior U.S. Pat. Nos. 3,865,106 and 3,945,378 disclose a ventilation circuit wherein the inspiratory conduit is concentrically within the expiratory conduit, to the end that there is reduced heat loss in the inspiratory conduit and thus less condensation therein. FIG. 5 illustrates an embodiment of the invention to permit this arrangement of the conduits. Here there is a manifold, generally 100, which replaces the manifold 15 of FIG. 1 and a fitting in the form of a manifold, generally 101, which replaces the patient "Y" 18. The conduits 16' and 17' correspond to the conduits 16 and 17 except that they are concentrically arranged.

Manifold 100 is columnar in form and has an entrance tube 102 which defines the inhalation chamber 103. The upper end of tube 102 is sized to receive leg 25 of elbow 14 and has an annular ridge 24 for engagement by clips 27. A side tube 104 communicates with chamber 103 and serves as an inspiratory conduit connection for inspiratory conduit 16'. An annular enclosure or tube 106 about the lower part of entrance tube 102 defines an exhalation chamber 107 between it and the entrance tube. Enclosure 106 has a lower portion 108 connecting to the valve 20 in the same manner described with respect to FIG. 1. A side tube 109 is concentric with tube 104 and provides a connection for the exhalation tube 17'. The bottom of the entrance tube 102 is closed by a wall 111 and this wall defines an orifice 112. Of course, orifice 112 corresponds to orifice 33 of the FIG. 1 embodiment. As in FIG. 2, valve 20 of FIG. 5 may be replaced with a solenoid operated valve 83.

The manifold 101 is primarily defined by concentric tubes 115 and 116. One end of each of these tubes forms a connection for the conduits 16' and 17', respectively. At the other end the tube 115 has a portion 117 extending beyond collar 118 and sized to be received within and engage the patient elbow 19. Like the portion 48 of "Y" 18 it has an annular ridge to be engaged within groove 89 of the elbow. Collar 118 corresponds to collar 47 of the "Y". Adjacent the collar is a wall 119 which closes that end of the external tube 116. Immediately inside of this wall the inner tube 115 has a plurality of openings 121 to provide comparatively free fluid communication between the two tubes. The sum of the areas of the openings should be about at least as great as the cross-sectional area available for airflow within the conduits 16' and 17' so that no flow restriction occurs. Tubes 122 and 123 functionally correspond to tubes 51 and 52 and provide access ports communicating with the interior of inhalation tube 115. That is, the port of tube 122 will receive a thermometer 124 while the port of tube 123 will receive a temperature control probe 125 connected to the ventilator 10. When not in use, they are closed with caps corresponding to those identified by the numbers 53 and 54 in FIG. 1. Elbow 127 communicates with the exhalation passageway and functionally corresponds to elbow 55 of FIG. 1. It is connected by a suitable length of tubing leading to the ventilator 10 thereby permitting the monitoring of the pressure. A tube 128 provides a port communicating with the inhalation passageway defined by tube 115. This port permits a medication nebulizer to be added to the circuit adjacent the patient end thereof (the nebulizer not being shown in the drawings but being conventional). When not in use it is closed by a cap corresponding to cap 53.

The operation of the embodiment of FIG. 5 is the full equivalent of the operation described with respect to the FIG. 1 embodiment. The ventilator forces the air to the patient in a pulse through the passageway defined by inhalation chamber 103, inspiratory conduit 16', tube 115 and elbow 19. The exhalation flow of air and carbon dioxide is from the elbow 19 through the openings 121 and into the exhalation passageway existing beween the tubes 16' and 17'. This exhalation passageway leads to the exhalation chamber 107 and thus to the valve 20, which of course is open during exhalation. Since the exhalation and exhalation passageways freely communicate with each other through openings 121 there is thus substantially no resistance and for all practical purposes the air pressures existing in chambers 103 and 107 are equal. As a consequence, there is no significant airflow through orifice 112 due to its comparatively high resistance. At the same time liquid accumulations in the inhalation chamber 103 will pass by gravity through the orifice into the exhalation chamber 107 and then exit through the valve 20 into the discharge tube 21 and the collection container 81.

I claim:

1. A method of condensate removal from a ventilation circuit for a patient which circuit comprises an inspiratory passageway through which conditioned air is delivered to a patient from a ventilator and an expiratory passageway leading from the patient and through which the patient's exhaled air is discharged through a valve having an inlet and an outlet and which is controlled by the ventilator to be opened and closed during selective modes of patient ventilation, said method comprising the steps of:

adjacent the ventilator providing an inhalation chamber in the inhalation passageway;

providing an exhalation chamber in the expiratory passageway and below the inhalation chamber;

adjacent the patient providing a first fluid communication between the two passageways;

providing a second fluid communication from the lower part of the inhalation chamber into the exhalation chamber wherein said second fluid communication has a substantially higher resistance to fluid flow therethrough as compared to the resistance existing through the passageways and the first fluid communication;

connecting the inlet of the valve to a lower part of the exhalation chamber;

draining condensate in the inhalation passageway into the inhalation chamber from where it will drain through the second fluid communication into the exhalation chamber;

draining the condensate in the expiratory passageway into the exhalation chamber; and draining the condensate in the exhalation chamber through the valve when open;

whereby the comparatively high resistance of the second fluid communication will effectively retard the flow of gas therethrough during the ventilation cycle due to the pressures in the chambers being otherwise equalized through the first fluid communication and the passageways connecting that first fluid communication with the chambers respectively.

2. A condensate removal system for use with a ventilation circuit extending between a patient and a ventilator having means for conditioning the air, wherein said circuit includes a manifold having an interior chamber and including internal wall means dividing the interior chamber of the manifold into an inhalation chamber having a lowermost portion and an exhalation chamber having a lowermost portion with the lowermost portion of the inhalation chamber being positioned above the lowermost portion of the exhalation chamber, said manifold having a lowermost portion communicating with the lowermost portion of said exhalation chamber and an exhaust conduit connection in that lowermost portion, an air-supply conduit having one end connected to said inhalation chamber and the other end adapted to be connected to the ventilator, a patient inspiratory conduit connected to the manifold and communicating with the inhalation chamber above the lowermost portion thereof, a patient expiratory conduit connected to the manifold and communicating with said exhalation chamber above the lowermost portion thereof, a discharge conduit connected to the exhaust conduit connection of the manifold, conduit means adjacent the patient and to which the inspiratory and expiratory conduits are connected with the conduit means providing fluid communication between the inspiratory and expiratory conduits, and valve means mounted in the manifold for controlling the flow of fluid from the expiratory chamber to the discharge conduit, said valve means adapted to be connected to the ventilator for timing the opening and closing of the valve means in accordance with selected modes of patient ventilation, said condensate removal system being characterized by:

said valve means being positioned in the manifold between the lowermost portion of the exhalation chamber and said lowermost portion of the manifold to control the flow of fluid therebetween, said manifold having air-supply conduit and inspiratory conduit connections to which said air-supply conduit and inspiratory conduit are connected and communicate with said inhalation chamber and an expiratory conduit connection to which said expiratory conduit is connected and communicates with said exhalation chamber, and said wall means including a lower wall portion defining an orifice forming a fluid communication between the inhalation and exhalation chambers;

whereby liquid accumulating in the exhalation conduit will drain into the exhalation chamber and liquid accumulating in the inhalation chamber will drain through the orifice into the exhalation chamber and thence pass through the valve means, when open, to the exhaust conduit connection, and said orifice presents a substantial resistance to the flow of air between the two chambers as compared to the resistance to the flow of air between the two chambers that exists through the inspiratory and expiratory conduits and their fluid communication at the conduit means to the end that the orifice is virtually closed to the passage of air during normal operation of the ventilation circuit.

3. A condensate removal system as set forth in claim 2, wherein the manifold is in the form of a column adapted to be positioned vertically with an upper end and a lower end, said wall means extending transversely across the column intermediate the upper and lower end whereby an upper part of the column forms the inhalation chamber and a part of the column below the wall means forms the exhalation chamber.

4. A condensate removal system as set forth in claim 3, wherein the inspiratory conduit and expiratory conduit connections are on a common side of the column and each extends outwardly from the column in an upwardly direction.

5. A condensate removal system as set forth in claim 2 and for use with a circuit wherein the inspiratory and the expiratory conduits are concentric with the inspiratory conduit inside the expiratory conduit, said system being further characterized by:

said manifold including two tubes each having an upper part, one of said tubes extending into the other of said tubes and at least in part being the wall means with the inhalation chamber being within the one tube and the exhalation chamber being outside the one tube and inside the other tube, said one tube having a bottom end that forms a wall thereacross and being said lower wall portion defining said orifice, said expiratory conduit connection extending from a side of said upper part of the other tube, said inspiratory conduit connection extending from the one tube and concentrically through the expiratory conduit connection.

6. In a ventilation circuit apparatus extending between a patient and a ventilator having means for conditioning the air, wherein said circuit includes a manifold having an interior chamber and including internal wall means dividing the interior chamber of the manifold into an inhalation chamber having a lowermost portion and an exhalation chamber having a lowermost portion with the lowermost portion of the inhalation chamber being positioned above the lowermost portion of the exhalation chamber, said manifold having a lowermost portion communicating with the lowermost portion of said exhalation chamber and an exhaust conduit connection in that lowermost portion, an air-supply conduit having one end connected to said inhalation chamber and the other end connected to the ventilator, a patient inspiratory conduit connected to the manifold and communicating with the inhalation chamber above the lowermost portion thereof, a patient expiratory conduit connected to the manifold and communicating with said exhalation chamber above the lowermost portion thereof, a discharge conduit connected to the exhaust conduit connection of the manifold, conduit means adjacent the patient and to which the inspiratory and expiratory conduits are connected with the conduit means providing fluid communication between the inspiratory and expiratory conduits, and valve means mounted in the manifold for controlling the flow of fluid from the expiratory chamber to the discharge conduit, said valve means being connected to the ventilator for timing the opening and closing of the valve means in accordance with selected modes of patient ventilation, the improvement comprising:

said valve means being positioned in the manifold between the lowermost portion of the exhalation chamber and said lowermost portion of the manifold to control the flow of fluid therebetween, said manifold having air-supply conduit and inspiratory conduit connections to which said air-supply conduit and inspiratory conduit are connected and communicate with said inhalation chamber and an expiratory conduit connection to which said expiratory conduit is connected and communicates with said exhalation chamber, and said wall means including a lower wall portion defining an orifice forming a fluid communication between the inhalation and exhalation chambers;

whereby liquid accumulating in the exhalation conduit will drain into the exhalation chamber and liquid accumulating in the inhalation chamber will drain through the orifice into the exhalation chamber and thence pass through the valve means, when open, to the exhaust conduit connection, and said orifice presents a substantial resistance to the flow of gas between the two chambers as compared to the resistance to the flow of gas that exists through the inspiratory and expiratory conduits and their fluid communication at the conduit means adjacent the patient to the extent that the orifice is virtually closed to the passage of gas during normal operation of the ventilation circuit.

7. In an apparatus as set forth in claim 6, and wherein there is a patient conduit extending from the conduit means, the further improvement comprising:

said conduit means including a tubular portion extending along an axis and having two ends, at one of said ends said portion defining a connection for the expiratory conduit, a first angular portion extending outwardly away from said axis at the other end of said tubular portion, said first angular portion having a distal end forming a connection for the patient conduit, and a second angular portion extending outwardly from said axis at a location intermediate the ends of the tubular portion, said second angular portion having a distal end defining a connection for the inspiratory conduit;

means defining a port for suctioning and other procedures at said other end of said tubular portion and linearly opposite from first angular portion;

a cap for said suction port; and means for releasably engaging said cap and the port defining means, with the cap when so engaged occluding said suction port.

8. In an apparatus as set forth in claim 7, and wherein the ventilator has a temperature control probe and an airway pressure monitor and wherein a thermometer is employed to detect the air temperature entering the patient conduit, said apparatus being further characterized by:

said second angular portion having two ports therein, one adapted to receive the thermometer and the other adapted to receive the ventilator temperature control probe, and said tubular portion having a port therein adapted for connection to said airway pressure monitor; and including occluding means releasably engaging said portions and occluding the three last-mentioned ports.

9. In an apparatus as set forth in claim 7, wherein
said tubular portion is formed in two telescopically fitted parts one of which has an annular groove and the other of which has an annular ridge seated in said groove whereby said two parts are rotatable with respect to each other; and
said first angular portion is formed in two telescopically fitted components one of which has an annular groove and the other of which has an annular ridge which is seated in the groove of said one component whereby said two components are rotatable with respect to each other;
whereby said conduit means has freedom of rotational movement in two planes transverse to each other while minimizing the risk of accidental separation.

10. In an apparatus as set forth in either of claims 6 or 7 and wherein said ventilator has a generally horizontal, rigid discharge duct through which the conditioned air is delivered, the further improvement
wherein said air supply conduit comprises a relatively rigid elbow having a first leg of a size to be structurally mated with said discharge duct and a second leg extending vertically downward from the first leg, said second leg being adapted to be structurally mated with said air-supply connection of said manifold; and
including latch means on said second leg and said air-supply connection for releasably holding the two together while permitting manifold to be rotated with respect to the second leg about a generally vertical axis;
whereby the manifold is supported by the ventilator and held in the desired vertical position.

11. In an apparatus as set forth in any of claims 6 through 8 wherein said conduit means includes means for providing freedom of rotational movement in two planes, which planes are at approximately right angles to each other.

12. In an apparatus as set forth in claim 6, wherein said conduit means comprises two components releasably mated together at a respective end of each, a first of said ends being telescopically received in the second of said ends with walls of each in juxtaposition to each other, one of said walls having an annular groove and the other of the walls having an annular ridge seated in said groove to releasably engage said components.

13. In an apparatus as set forth in claim 12, and for use with a length of tubing of a given internal diameter to form a dead space, the further improvement comprising:
said second end having an external diameter only slightly greater than said internal diameter so that said tubing may be slipped over said second end to frictionally engage said second end; and
the component having the first of said ends including a tubing receiving portion having an external diameter so that said tubing may be slipped over said second end tubing receiving portion to frictionally engage said tubing receiving portion;
whereby with said two components separated from each other a length of tubing to form the desired dead space may be slipped over and engage the two ends to form a connection therebetween.

14. In an apparatus as set forth in claim 6 and for use with an adjustable patient circuit support arm having an engaging means on a distal end thereof, the further improvement comprising:
a support member having clips engaging the inspiratory and expiratory conduits respectively, each clip being of a conformation to encircle and engage a part of a circumference of the respective conduit and being slidable along the respective conduit in a direction longitudinally of the conduit, said support member having means attached to the clips and adapted to be engaged by said engaging means.

15. An apparatus as set forth in claim 6, wherein said valve means comprises:
a valve body, a wall in the valve body defining a valve seat about a valve opening, at one side of said seat there being a space which is a part of the expiratory chamber and at the other side of said seat there being a space which is a part of said lowermost portion of the manifold, a resilient diaphragm extending across said seat and having a first side in light contact with the seat so as to normally permit fluid flow between it and the seat and out of the expiratory chamber while acting as a check valve to block fluid flow into the expiratory chamber from the exhaust conduit connection and a second side facing away from said seat, a valve cover over said second side of said diaphragm and with said diaphragm defining a pressure chamber, the arrangement being such that when air pressure is supplied to said pressure chamber said diaphragm is urged against said seat in the valve-closed position, said diaphragm being of a contrasting color and said cover being at least semitransparent whereby the operation of the diaphragm may be observed, said cover engaging said valve body in a manner making it removable only with difficulty,
whereby liquid collecting in said expiratory chamber will drain down to said one side of said seat and, when said valve is open, will drain by the diaphragm and thus into the lowermost part of the manifold.

16. In an apparatus as set forth in claim 6 and for use with an adjustable patient conduit support arm having an engaging means on a distal end thereof, the further improvement comprising:
a support member having means for engaging one of said patient conduits while being movable longitudinally thereof, said support member having means attached to the clips and adapted to be engaged by said engaging means.

17. In an apparatus as set forth in claim 6, and wherein there is a patient conduit extending from the conduit means, the further improvement comprising:
said conduit means including a pair of concentric tubes each having two ends, one end of the innermost tube being connected to the inspiratory conduit and a corresponding one end of the outermost tube being connected to the expiratory conduit, adjacent the other of its ends the innermost tube having a plurality of openings to provide fluid communication between the two tubes, said openings in the aggregate providing an area for the flow of fluid which is at least as large as the cross-sectional area available for the flow of fluid in the expiratory conduit, an elbow communicating with the other end of one of said tubes, and means closing the other end of the other of said tubes.

18. In an apparatus as set forth in claim 17, and wherein there is a patient conduit extending from the distal end of the elbow, and wherein the ventilator has a temperature control probe and an airway pressure monitor and wherein a thermometer is employed to detect the air temperature entering the patient conduit, said apparatus being further characterized by:
- said elbow having means located linearly opposite said distal end of the elbow and defining a port for suctioning and other procedures;
- a cap for said suction port;
- means releasably engaging said cap and said port defining means, with the cap when so engaged occluding said suction port;
- said innermost tube having means extending outside the outermost tube and defining two ports in the innermost tube, one adapted to receive the thermometer and the other adapted to receive the ventilator temperature control probe, and also having means extending outside the outermost tube and defining a port adapted for connection to said airway pressure monitor; and
- including occluding means releasably engaging said means extending outside the outermost tube and occluding the three last-mentioned ports.

* * * * *